(12) United States Patent
Silva et al.

(10) Patent No.: US 9,291,834 B2
(45) Date of Patent: Mar. 22, 2016

(54) SYSTEM FOR THE MEASUREMENT OF THE INTERPUPILLARY DISTANCE USING A DEVICE EQUIPPED WITH A DISPLAY AND A CAMERA

(71) Applicant: REVERSE ENGINEERING, LDA, Lisbon (PT)

(72) Inventors: Cesar Augusto dos Santos Silva, Lisboa (PT); Andre Filipe Marques da Silva, Almada (PT)

( * ) Notice: Subject to any disclaimer, the term of this patent is extended or adjusted under 35 U.S.C. 154(b) by 340 days.

(21) Appl. No.: 14/089,552

(22) Filed: Nov. 25, 2013

(65) Prior Publication Data

US 2014/0152956 A1 Jun. 5, 2014

Related U.S. Application Data

(63) Continuation-in-part of application No. 14/122,169, filed as application No. PCT/IB2013/051037 on Feb. 8, 2013.

(51) Int. Cl.
  *A61B 3/10* (2006.01)
  *G02C 13/00* (2006.01)
  *A61B 3/11* (2006.01)

(52) U.S. Cl.
  CPC ............. *G02C 13/005* (2013.01); *A61B 3/111* (2013.01)

(58) Field of Classification Search
  CPC ........... A61B 3/113; A61B 3/111; A61B 3/11
  USPC .......................................... 351/204, 246, 206
  See application file for complete search history.

(56) References Cited

U.S. PATENT DOCUMENTS

| | | |
|---|---|---|
| 3,495,897 A | 2/1970 | Deforges |
| 4,845,641 A | 7/1989 | Hagiwara et al. |
| 6,095,650 A | 8/2000 | Gao et al. |
| 6,261,248 B1 | 7/2001 | Takaishi et al. |
| 6,535,223 B1 | 3/2003 | Foley |
| 6,791,584 B1 | 9/2004 | Xie |

(Continued)

FOREIGN PATENT DOCUMENTS

| | | |
|---|---|---|
| CN | 102278978 | 12/2011 |
| DE | 10007705 | 2/2000 |

(Continued)

OTHER PUBLICATIONS

Espacenet, English Machine Translation of JP2004220069, Aug. 5, 2004.

(Continued)

*Primary Examiner* — Hung Dang
(74) *Attorney, Agent, or Firm* — Selwyn S. Berg (57) ABSTRACT

A system for measuring the interpupillary distance of two eyes of a face using a device equipped with a display and a camera. For example, a guide marker (or guide markers) is displayed on a reflective display, and an image is captured using the camera when the reflection of the face is aligned with the guide marker. A stereo pair is created using the camera image and the reflection of the face on the display, and the interpupillary distance is determined by comparing the three-dimensional positions of the two eyes. The device is capable of calibration using a calibration object to detect the distance between the guide marker on the display and the camera. A facial recognition engine is employed in some cases to detect the eyes or other points on the camera image.

22 Claims, 9 Drawing Sheets

(56) References Cited

U.S. PATENT DOCUMENTS

| | | | |
|---|---|---|---|
| 6,847,383 B2 | 1/2005 | Agnew | |
| 7,219,995 B2 | 5/2007 | Ollendorf | |
| 7,322,697 B2 | 1/2008 | Jojiki | |
| 7,404,639 B2 * | 7/2008 | Nishihira | A61H 5/00 351/200 |
| 7,665,843 B2 | 2/2010 | Xie | |
| 7,740,355 B2 | 6/2010 | Sessner et al. | |
| 8,231,220 B2 | 7/2012 | Baranton | |
| 2003/0123026 A1 | 7/2003 | Abibol et al. | |
| 2004/0004633 A1 | 1/2004 | Perry et al. | |
| 2005/0265604 A1 | 12/2005 | Yuasa | |
| 2007/0118428 A1 | 5/2007 | Akiyama et al. | |
| 2008/0201641 A1 | 8/2008 | Xie | |
| 2010/0220285 A1 | 9/2010 | Simmonds | |
| 2011/0242481 A1 | 10/2011 | Wada et al. | |
| 2011/0267578 A1 | 11/2011 | Wilson | |
| 2011/0317031 A1 | 12/2011 | Honda | |
| 2012/0016763 A1 | 1/2012 | Kirschner | |
| 2012/0257162 A1 | 10/2012 | Encaoua et al. | |
| 2012/0274902 A1 | 11/2012 | Baranton et al. | |
| 2013/0076884 A1 | 3/2013 | Choukroun | |

FOREIGN PATENT DOCUMENTS

| | | |
|---|---|---|
| FR | 1506352 | 12/1967 |
| GB | 2449855 | 12/2008 |
| JP | 2002034918 | 2/2002 |
| JP | 2004220069 | 8/2004 |
| KR | 100984550 | 9/2010 |
| WO | 2009007731 | 1/2009 |
| WO | 2011042623 | 4/2011 |
| WO | 2011113936 | 9/2011 |
| WO | 2011074769 | 11/2011 |
| WO | 2012022380 | 2/2012 |

OTHER PUBLICATIONS

Google Patents, English Machine Translation of CN102278978, Dec. 14, 2011.

Google Patents, English Machine Translation of WO2012022380, Feb. 23, 2012.

Warren Robinett et al., A Computational Model for the Stereoscopic Optics of a Head-Mounted Display, SPIE vol. 1457 Stereoscopic displays and Applications II, pp. 140-160, 1991.

Elmar T. Schmeisser et al., Analysis of Cardlab Data for Interpupillary and Vertex Distance: Notes on the Construction of an "Eye-Box", United States Air Force Research Laboratory, pp. 1-17, Jul. 1998.

Carlos Hitoshi Morimoto, Automatic Measurement of Eye Features Using Image Processing, Departamento de Ciencia da Computacao, pp. 1-11, Dec. 31, 2009.

Andrew Winters, Bringing Eyewear Measurement Into the 21st Century, VCPN, http://www.totallyoptical.com/...7027421841978F18BE895F87F791&tier=4&id=E6466401ABEF46358A158E6049F93E07&AudID=28EBA89F5F874675BCE10DE3DCF0D05B, pp. 1-2, Oct. 2008.

Optician, iPhone enables online buyers to measure PD, http://www.opticianonline.net/Articles/2010/08/27/26151/iPhone+enables+online+buyers+to+measure+PD+.html, pp. 1-2, Aug. 27, 2010.

Shay Rootman, YouTube Video, Mychic Augemented Reality Pupils Distance PD measure tool, http://www.youtube.com/watch?v=NEx3BiiXbZc, uploaded on Mar. 29, 2012.

TechWench, New iPhone App Solves Worries About PD When Buying Glasses Online, http://www.techwench.com/new-iphone-app-solves-worries-about-pd-when-buying-glasses-online, pp. 1-10, Nov. 21, 2011.

Vistech Projects, Android App: Partometer-Camera Measure, http://www.4androidapps.net/apps/partometer-camera-measure-download-198010.html, pp. 1-13, Mar. 13, 2012.

Rob Dewhurst, Android App: Pupil Meter, https://play.google.com/store/apps/details?id=air.PupilMeterAnd, pp. 1-2, Dec. 13, 2010.

Just Eyewear, Pupilmeter, http://www.justeyewear.com/pupilmeter, pp. 1-2, Feb. 9, 2011.

Rob Dewhurst, Ipad App: Pupilo Meter Pro, https://itunes.apple.com/us/app/pupil-meter-pro-for-ipad/id399778692, pp. 1-2, Dec. 5, 2011.

Espacenet, English Abstract of JP2002034918, Feb. 5, 2002.

Google Patents, English Abstract and English Machine Translation of DE10007705, Feb. 19, 2002.

Swennen et al., A new method of 3-D cephalometry Part I: The anatomic Cartesian 3-D reference system, The Journal of Craniofacial Surgery, pp. 314-325, Mar. 2006. (Only abstract provided).

* cited by examiner

SYSTEM FOR THE MEASUREMENT OF THE INTERPUPILLARY DISTANCE USING A DEVICE EQUIPPED WITH A DISPLAY AND A CAMERA

CROSS-REFERENCE TO RELATED APPLICATIONS

This document claims priority as a continuation-in-part of U.S. National Stage application Ser. No. 14/122,169 filed 25 Nov. 2013 and co-pending International Patent Application No. PCT/IB2013/051037, file 8 Feb. 2013, and to Portuguese Patent Application No. PT106430, filed 3 Jul. 2012, each of which are hereby incorporated by reference in their entirety.

BACKGROUND

The following relates generally to devices, systems, and methods used to determine the distance between facial features, particularly the interpupillary distance.

Proper prescription and sizing of corrective eyeglasses requires measurement of several biometric dimensions of the face and optical system of the patient. Personalized lenses are crafted not only using the amount of corrective power required to assist the patient's eyes in focusing on objects, but also using precise measurements of the patient's facial features, including the distance between the centers of each of the pupils of the patient's eyes, also known in ophthalmological terms as the interpupillary distance. The distance is formally defined as the distance from the optical axis of one eye to the optical axis of the other eye, where the optical axis extends through the center of each pupil normal to the surface of the eye. Knowing this distance, the center of the corrective lens can be oriented directly in front of each eye along these axes, leading to clearer and more comfortable vision. An incorrect measurement of the interpupillary distance (even by two millimeters) creates a misalignment of the ophthalmic lenses relative to the eyes, leading to imperfect vision and eye strain.

Other biometric data used in lens design include the distance from the patient's nose to the optical axis of the eye, known as mono-pupillary distance, and the distance from the center of the pupil to the lens, referred to as the vertex distance. The inclination angle between the direction of the lens and the optical axis may also be significant in providing healthy vision correction. The interpupillary distance may also be determined depending on the position of the pupils at near or far vision, which may be referred to as the near interpupillary distance or the far interpupillary distance.

Existing systems and methods for measuring biometric data such as the interpupillary distance are complex and costly, and are mainly only usable by specialized, trained technicians, optometrists, and ophthalmologists in clinics or other offices. The systems used are quite accurate, measuring distances with error of less than 1 millimeter, but use specialized, sophisticated machinery and often require extra objects to be placed above the patient's face or over the frame. They are also expensive to use, requiring the active participation and time of these trained specialists to achieve the desired results and requiring the patient to travel to the office or clinic to gather the measurements.

To address some of these issues, various systems and methods have been presented to use cameras and other common devices to measure the patient's interpupillary distance remotely and without need for interaction of a trained specialist. For example, systems have been devised where one or more objects with predefined markers such as ruler markings are placed on or around the face and a sequence of images of the face and objects are captured and compared to each other to determine the necessary dimensions. However, in these systems the presence of the marker objects is crucial to obtain a geometric relationship between the pictures, and the user is expected to take pictures of himself or herself in various predefined poses which may be difficult to obtain alone while maintaining accuracy of the measurement. It is common for these methods to produce measurement error of 3 millimeters or more due to parallax errors and due to misuse of the marker objects, so they are generally discouraged by optometrists.

In other systems, no artifact or object is required on or around the face. Instead, the patient makes a predetermined set of movements, and the system applies a statistical calculation which is based on an iterative optimization algorithm run on the set of images gathered for estimating the distance to the camera, the interpupillary distance, the focal length of the camera, the radius of the eyeball and pupil sizes. The effectiveness of these systems is limited, since there is a computational burden of analyzing the images of the patient's movements, the patient's movements can be difficult to control. Furthermore, these systems often rely on automatic detection of the circle around the pupil, which can be difficult since that relies on sophisticated methods of detection and a high camera resolution.

In recent years, the market for online sale of ophthalmic lenses and frames has increased significantly, and with this new market there is a need for accurate, remote detection of the interpupillary distance. Existing methods of determining the interpupillary distance may be too expensive, too inaccurate, or too unreliable, or require the patient to go to an ocular specialist, thereby defeating a main advantage of online sales—buying without the physical presence of the customer. Thus, there is a need for an accurate, inexpensive, simple system that can be used by patients (to obtain the patient's interpupillary distance) without need of specialized artifacts or specialized technicians in this market and others.

SUMMARY

According to at least one embodiment, a method of determining a distance on a human body using an electronic device is described. The method may include displaying at least one guide marker on a display. The display may have a reflective surface. The method may also include capturing an image via a camera associated with the display. This image may include two points on the body (e.g., the human body, such as on a face). The image may be captured when a reflection of the two points is aligned with the at least one guide marker. The method may also include determining a three-dimensional position of each point based on a stereo pair of (a) the image and (b) the reflection of the two points aligned with the at least one guide marker, and then may calculate the distance between the two points by comparing the three-dimensional positions of each point.

In another embodiment, the two points on the body are, specifically, the centers of each of two pupils of a pair of eyes of a face. The distance between the two points may be the interpupillary distance. When the distance is an interpupillary distance, the capturing step may be repeated to capture a plurality of images, wherein each of the plurality of images correspond with different interpupillary distances. These different distances may, for example, correspond with the far interpupillary distance and the near interpupillary distance.

In another embodiment, the method comprises determining calibration information of the camera. For example, this may include the focal length of the camera, the distance between the camera and portions of the device, such as the at least one guide marker shown on the display. Determining the calibration information may include capturing an image via the camera, wherein the image includes a calibration object having a known geometric relationship to the camera and the display, then detecting a calibration point or pattern on the calibration object in the image, and comparing the calibration point or pattern of the image to predefined calibration point data to determine the spatial distance between the at least one guide marker and the camera and/or the field of view of the camera. The calibration object may include a pattern of calibration points, and the calibration point is detected by detecting at least a portion of the pattern of calibration points.

In some embodiments, the method may comprise a step of detecting the two points in the image. This may involve detecting the two points by engaging a facial recognition engine.

The three-dimensional position of each point on the body may be given by an intersection of a projection ray and a plane extending normal to the reflective surface through at least a portion of the at least one guide marker. These projection rays pass through one of the points (e.g., the pupils of the face) and the camera where the points are coincident with the plane. Here, at least one guide marker may include a line on the display and the line is coincident with the plane defined by the guide marker.

In another embodiment, a computing device is configured to determine a distance on a human body, wherein the device comprises a processor, memory in electronic communication with the processor, and computer readable instructions stored by the memory that cause the processing circuit to perform a method. The method may include displaying at least one guide marker on a display which may have a reflective surface. The method may also include capturing an image via a camera associated with the display. This image may include two points on the body (e.g., the human body, such as on a face). The image may be captured when a reflection of the two points is aligned with the at least one guide marker. The method may also include determining a three-dimensional position of each point based on a stereo pair of (a) the image and (b) the reflection of the two points aligned with the at least one guide marker, and then may calculate the distance between the two points by comparing the three-dimensional positions of each point.

In some embodiments, the computing device's instructions may include that the two points on the body are the centers of each of two pupils of a pair of eyes of a face, and that the distance between the two points is the interpupillary distance. The camera may repeatedly capture images to produce a plurality of images, where each of the images correspond with different interpupillary distances.

In some embodiments, the instructions may include determining calibration data of the camera. This may entail capturing an image via the camera, where the image including a calibration object has a known geometric relationship to the camera and the display; detecting a calibration point on the calibration object in the image; and determining the spatial distance between the at least one guide marker and the camera and/or a field of view of the camera by comparing the calibration point of the image to predefined calibration point data. The calibration object in these configurations may include a calibration pattern, with the calibration point being detected by detection of the calibration pattern.

In other embodiments, the instructions may include detecting the two points in the image captured by the camera. For example, detecting the two points may engage a facial recognition engine to analyze an image for facial features.

The three-dimensional position of each point may be given by an intersection of a projection ray and plane extending normal to the reflective surface of the display through at least a portion of the at least one guide marker. Thus, projection rays may pass through the points and the camera where the points are coincident with the plane. In such embodiments, the guide marker may comprise a line on the display which is coincident with the plane defined by the guide marker.

In another embodiment, a computer-program product is described which may determine, by a processor, a distance on a human body. The computer program product may include or be embodied by a non-transitory computer-readable medium storing instructions thereon, where the instructions are executable by the processor to: (a) display at least one guide marker on a display, the display having a reflective surface; (b) capture an image via a camera associated with the display, the image including two points on a body, wherein when the image is captured a reflection of the two points is aligned with the at least one guide marker; (c) determine a three-dimensional position of each point based on a stereo pair, the stereo pair including the image and the reflection of the two points aligned with the at least one guide marker; and (d) calculate the distance between the two points by comparing the three-dimensional positions of each point.

The foregoing and other features, utilities and advantages of the invention will be apparent from the following more particular description of a preferred embodiment of the invention as illustrated in the accompanying drawings.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Systems and methods for determining the interpupillary distance (or another facial distance) using a camera and reflective display are disclosed herein. These systems and methods may allow a user to measure the interpupillary distance using a conventional device with a camera, a reflective display, and at least a low level of processing capacity, such as a smartphone, laptop computer, tablet, PDA, or other similar device.

In at least one embodiment, the screen surface of the device is reflective, and acts in some capacity as a mirror, allowing the user to see his or her own reflection. The user may align the centers of each pupil to a guide marker displayed on the screen, generating a condition where the user's eyes are in a common plane. The camera of the device may detect the user's pupils and estimate a projection ray between the camera and each pupil. A stereo pair of images may then be used to determine the positions of the pupils in three-dimensional space, from which positions the distance between the pupils can be accurately determined using simple geometric relationships. In some embodiments the profile, outline, or general shape of the face is all that is seen in the reflection.

Implementing these systems and methods may yield benefits including: eliminating the need for specialized equipment, eliminating the need for a specialized technician taking measurements, needing only a single photograph of a user without forcing a particular user motion or movement, ease of implementation on widely available consumer devices, and accuracy, with error of less than 1 millimeter in some cases, unlike many other approximated methods. Additional or alternative features and benefits will be discussed or will be apparent from the description of various embodiments and methods herein. The systems and methods disclosed herein are not limited to applications of optometry, but may also be extended to aesthetic, cosmetic and reconstructive medicine applications, such as aesthetic eyebrows, lips, hair, makeup, tattoos, and pre- and post-surgical cosmetic and reconstructive medicine.

Figure 1:
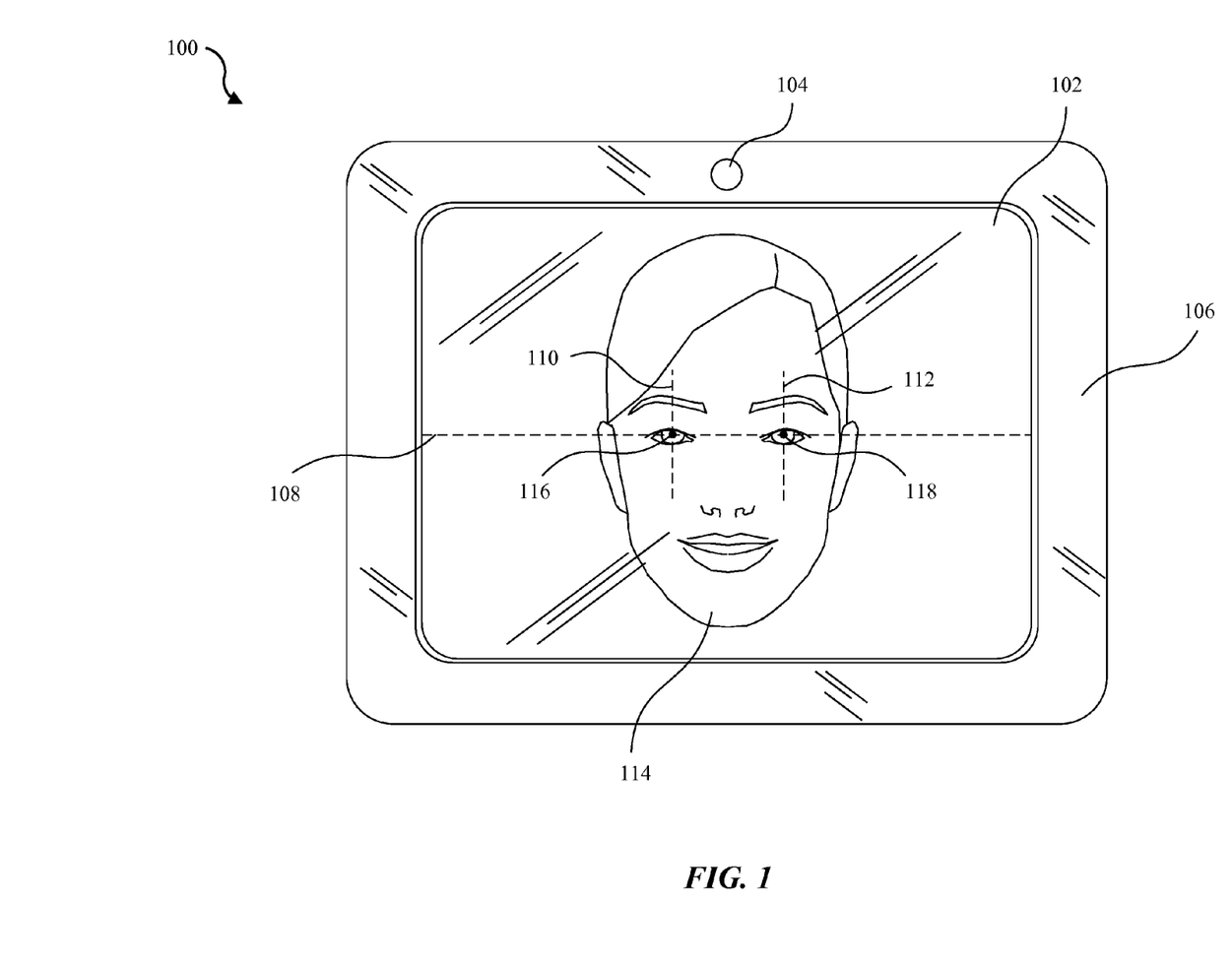
FIG. 1 shows a diagram of a mobile device showing a reflection of a user according to one embodiment of the disclosure.

Turning now to the figures in particular, FIG. 1 is a diagram showing a mobile device 100 according to one embodiment of the present systems and methods. The mobile device 100 may be referred to herein as a tablet computer or tablet, but may be a laptop computer, smartphone, personal computer, personal digital assistant, mobile phone, desktop computer, or other computing device.

The tablet may have a reflective screen, which may also be referred to as a reflective display 102. The display 102 may be a computer display, such as, for example, a common liquid crystal display (LCD), plasma screen, or similar technology capable of displaying images to a user facing the display 102.

The display 102 may be reflective due to the surface of the display 102 being a smooth, polished or glossy surface. For example, the display 102 may be composed in part of glass or a rigid acrylic, polycarbonate, or other glossy polymer construction. In some embodiments, the display 102 surface may include an at least partially mirrored surface, such as being mirrored due to silvering or another smooth metallic deposit on a side of the display 102 surface, provided that the user can still see images or other representations shown on the display 102. In some embodiments, the display 102 itself may not be reflective on its own, but a reflective film or panel is placed parallel to the surface of the display 102 between the display 102 and the user in a manner mimicking an inherently reflective display. A reflective film or panel may be beneficially positioned as close to the display 102 as possible to accurately simulate a mirror. The display 102 may beneficially be entirely flat, further ensuring an accurate mirror effect.

In some embodiments, the reflectivity of the display 102 may be less than the reflectivity of glass or another smoothly polished surface, or may be only partially reflective. For example, the display 102 may have a frosted surface, anti-glare coating, or similar surface treatment. In such embodiments, it may suffice that the surface of the display 102 is reflective enough to provide a reflection of the portions of the user needed for proper positioning of the device in relation to the user, as discussed in more detail in connection with FIG. 2. Displays of conventional mobile computing devices are commonly reflective enough to function as a mirror, such that it is possible to see the user's reflection on them, particularly when the background of the display is black and used under adequate light conditions.

The display 102 may be positioned in the tablet adjacent to a camera 104. In this embodiment, the camera 104 is integrated into a bezel 106 of the tablet surrounding the display 102, but the camera may be separate from the mobile device 100 or may be connected in other orientations on the bezel 106 or other portions of the device 100. For example, if the device 100 is a personal computer, the camera 104 may be positioned above or below the display 102. The camera 104 may face the user who is facing the display 102 and may be capable of capturing a depiction of the face of the user. In some configurations, the camera 104 may capture a depiction of the user when a shutter is triggered by the user, but in other configurations the camera 104 may collect an image after expiration of a timer or based on a feedback loop using the camera input, such as when a facial recognition software engine detects via the camera 104 that a user is properly positioned facing the mobile device 100. The camera 104 may beneficially have known focal length, distortion parameters, optical center, and other related characteristics.

The display 102 shows a plurality of guide markers 108, 110, 112 that may be lines extending across the display 102. The guide markers 108, 110, 112 may be composed of one or more markings on the display 102 that may be used to establish or fix the position of one or more features of the user's face when properly aligned with the reflection 114 of the user. In FIG. 1, guide marker 108 is shown as a dashed horizontal line and may be used to establish a horizontal plane aligning with the user's pupils, and guide markers 110, 112 are shown as vertical dashed lines intended to intersect the pupils of the reflection 114. In other configurations, the guide marker 108 may be a set of shapes or dots on the display that may be aligned with the user's features when a reflection 114 is seen on the surface of the display 102. For example, the guide marker 108 may be a pair of visible points (positioned to align with the center of the pupils of the user's reflection 114), two circles (positioned to be filled with the pupils' reflections), a line segment (for intersecting the center of the pupils), or any other equivalent geometric shape or design able to restrict the reflected pupil centers within a pre-established straight line or plane. By doing so, the reflection 114 of the user may have its pupils constrained within a known plane with respect to the device 100, as described in more detail in connection with FIG. 2. The guide markers 108, 110, 112 may beneficially be white or another light color when shown on the display 102 with the display 102 being black or another dark color, since it may be easier to see a reflection (e.g., reflection 114) on a dark display 102, and it may be easier to see the guide markers 108, 110, 112 when they contrast the darkness of the display 102. The display 102 may also be black due to being turned off completely and having a dark polarizer or other visible panel, or by having a backlight turned off. In some arrangements, the guide markers 108, 110, 112 may be superimposed on the display 102, such as being printed on a glass panel or other overlaid intermediate surface. Effects of double reflection due to multiple layers of glass present on the display 102 may be considered to be negligible when the layers are close together.

The reflection 114 of a user is shown in FIG. 1 as it would appear to a user positioned facing the tablet. It will be understood that the reflection 114 may appear as if the user were at least partially or somewhat reflected in a mirror, where the reflection 114 is a 1:1 representation of the user's face. Thus, the display 102 may have dimensions sufficient to display the portions of the user's face that are measured using the systems and methods disclosed herein. For example, when measuring the interpupillary distance, the reflection 114 on the display 102 may include the pupils of both eyes 116, 118. In such an embodiment where the pupils 116, 118 are measured, other features of the face such as the mouth or ears may not be required to be reflected on the screen 102. Additional features relating to the positioning of the mobile device 100 are described in connection with FIG. 2.

Figure 2:
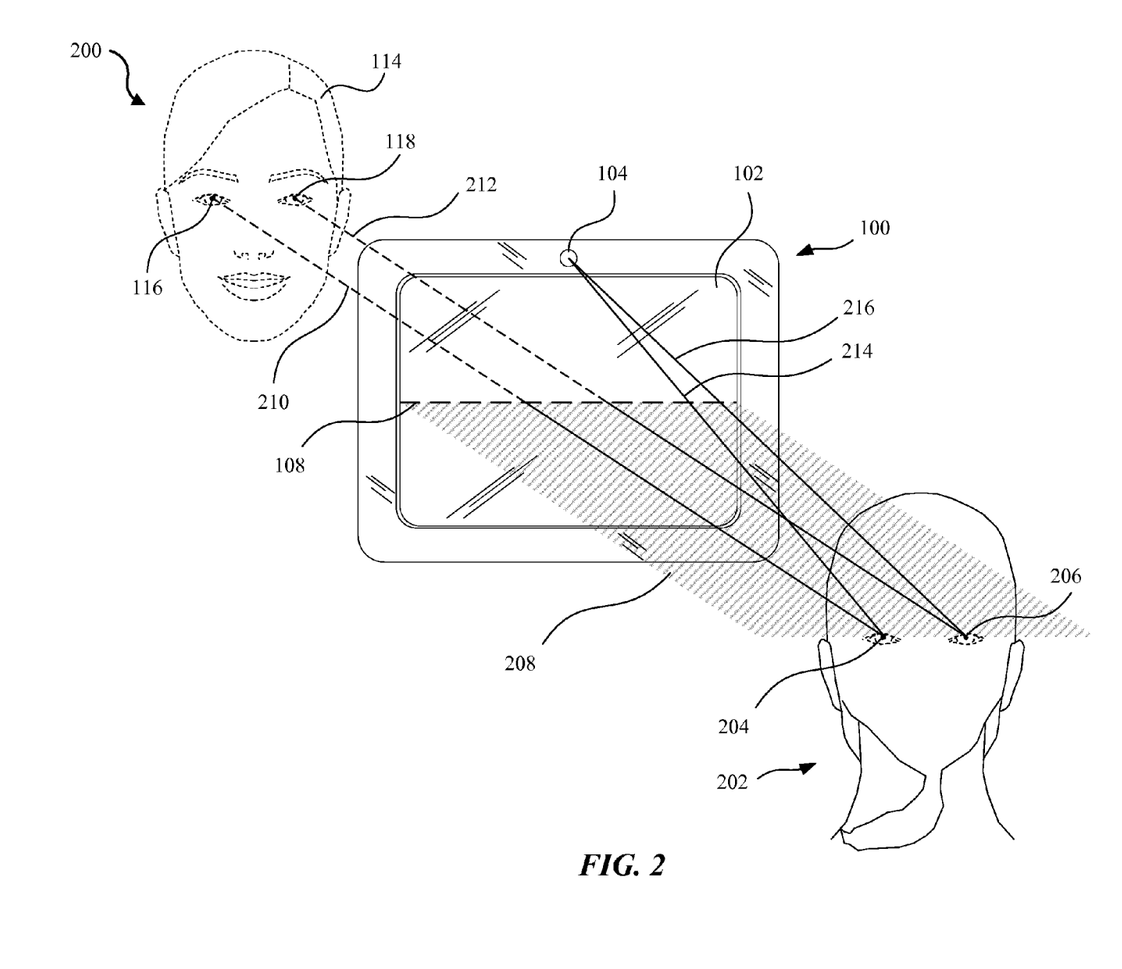
FIG. 2 shows a diagram of a user and reflection of the user positioned relative to a mobile device.

FIG. 2 is a diagram 200 showing an exemplary positioning of a user 202 with respect to a mobile device 100. The user 202 may be positioned in front of the mobile device 100, which may be a tablet computer, with the camera 104 and display 102 facing the user. The display 102 may show one or more guide markers (e.g., guide marker 108). The reflection 114 of the user is shown in this diagram behind the device 100 to represent how the reflection 114 would appear to the user 202 when looking into the display 102. When properly positioned, the left pupil 204 and right pupil 206 of the user 202 may fall within a plane 208 defined in part by the guide marker 108 due to the user 202 aligning the reflected left pupil 116 and reflected right pupil 118 with the guide marker 108 (e.g., as shown in FIG. 1). Thus, reference lines 210, 212 are in-plane with plane 208. These reference lines 210, 212 are not necessarily parallel. The plane 208 may be perpendicular to the display 102, but may also be oriented in a non-normal direction from the display 102.

With the user 202 in this position, the camera 104 may capture an image of the user 202. Using this image and the implied image of the user that can be assumed due to the alignment of the reflection 114 in the display 102 (as shown in FIG. 1), three-dimensional geometric projection rays 214, 216 may be constructed from the position of the camera 104 that intersect the plane 208 at the position of the pupils 204, 206 on the user's face. This geometric construction may be used to calculate the three-dimensional coordinates of the pupils 204, 206, which can then be used to determine the distance between the pupils 204, 206, which is the interpupillary distance of the user 202. Therefore, restricting the centers of the pupils 204, 206 to two points in the image may restrict the location of the centers of the two projection rays 214, 216, and the locations of the centers of the pupils can be found through the intersection of the rays and the projection plane 208.

In other embodiments, the three-dimensional position of any arbitrary points defined on the plane 208 may be determined, whether or not they belong to the user's face or belonging to a frame or lens placed over the user's face, provided that they are viewable by the camera 104. For example, it may be advantageous to determine the distance between the point on the axis of symmetry of the nasal dorsum, used to calculate the left and right nasal-pupillary distance, defined as the distance from the sagittal plane passing through this point to the center of the left and right pupils, respectively. In another example, it may be beneficial to determine the distance between the two inner extreme points of the left and right lenses of the user's eyewear, used to calculate the size of the bridge, which may be defined as the distance between the inner ends of the two lenses. Other example points may include the external points on the lenses or frame of corrective eyewear and/or the point on a lens that is intersected by the optical axis of the user, which may be used to calculate the vertex distance (the distance between that point on the lens and the center of the pupil. In some embodiments, these points must be detected manually by the user (see FIG. 3 and related description below) with their position calculated from the intersection of a projection ray of the point on an image captured by the camera 104 and the plane 208. In another example embodiment, the three-dimensional position of generic points on the face that have approximately the same distance apart as the interpupillary distance may be used in place of using the pupils as points.

Figure 3:
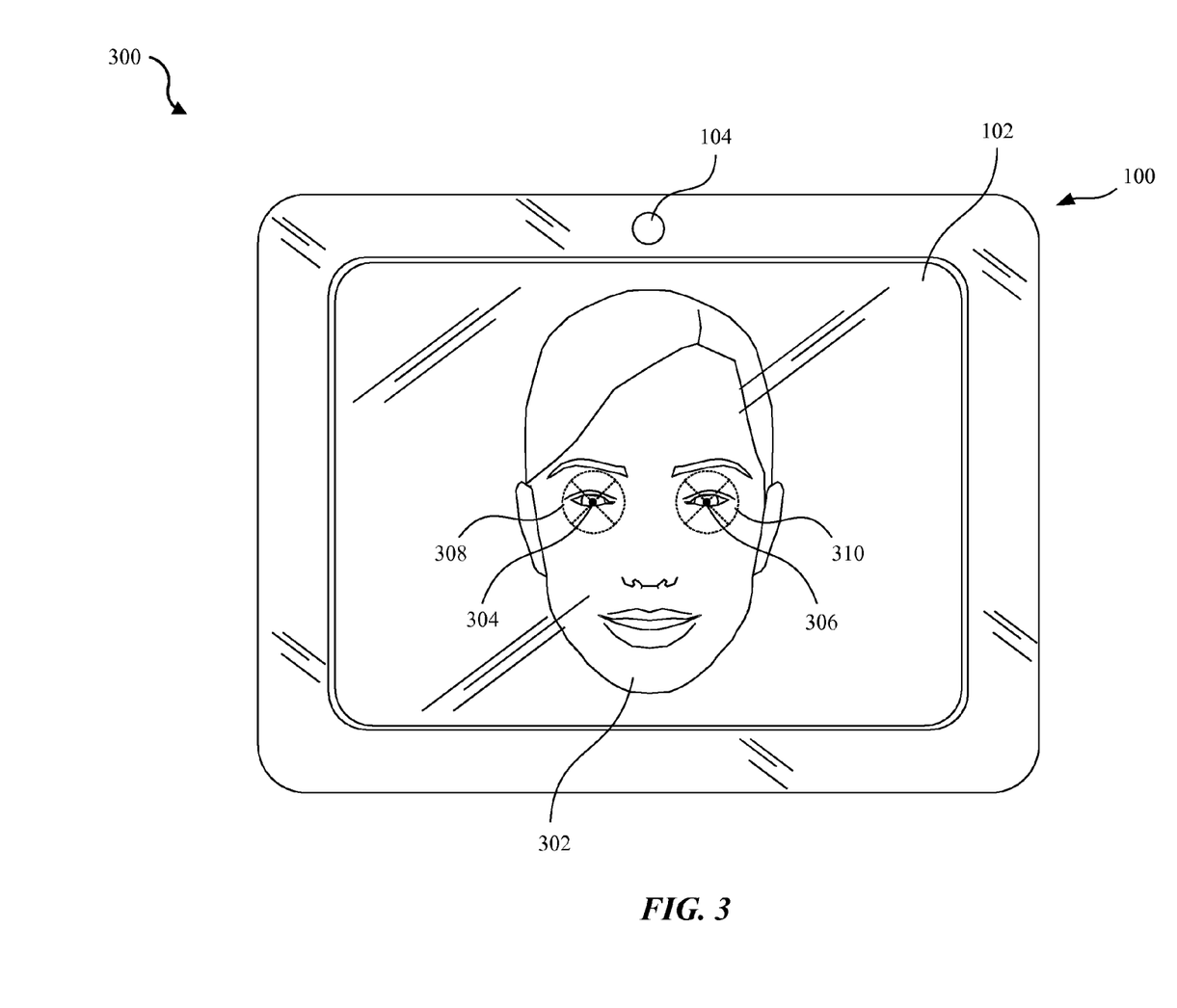
FIG. 3 shows a diagram of a mobile device displaying a captured image.

The determination of the three-dimensional position of the user's pupils 204, 206 may be dependent on detection or identification of the pupils 204, 206 within the image captured by the camera 104. FIG. 3 is a diagram 300 showing a mobile device 100 displaying an image 302 of the user that was captured by the camera 104. The image 302 of FIG. 3 therefore is different than the reflection 114 of FIG. 1 in that the display 102 is producing the image 302 for the viewer, but the reflection 114 is a reflection of ambient light on the display 102 surface and not a product of light generated by the display 102.

The image 302 may be presented on the display 102, as shown in FIG. 3. The user may indicate the location of the image pupils 304, 306 by positioning two pupil markers 308, 310 on the image pupils 304, 306. For example, the user may be prompted or instructed to touch the image pupils 304, 306 (e.g., on a touch screen device) or to drag the markers 308, 310 using an input device to cover the image pupils 304, 306. In this manner, the user may indicate the positions of the image pupils 304, 306 on the image 302. Based on the known relationship between the guide marker (e.g., guide marker 108) and properties of the camera 104, the distance between the markers 308, 310 positioned by the user may be translated into a physical, measureable interpupillary distance of the pupils 204, 206. The distance between the one or more guide marker on the display 102 and the camera 104 on the bezel 106 of the device 100 may be known or determined, and the field of view of the camera may be known or determined during the measurement process in order to obtain a more accurate measurement.

In some arrangements, a facial recognition engine may be employed to detect the image pupils 304, 306 in the image 302. For example, the facial recognition engine may be a software-based image analysis algorithm configured to detect facial features or related patterns on or around a face in an image. The facial recognition engine may thereby detect eyes on a face, and pupils in the eyes, and automatically determine the location of the image pupils 304, 306. The pupil markers 308, 310 may then be superimposed over the image pupils 304, 306 as detected by the engine and displayed on the display 102. In other arrangements, the image 302 may be stored by memory associated with the camera 104 and processed without being viewable by the user.

To illustrate how the interpupillary distance may be calculated, the following example may be useful. For a given interpupillary distance, the pupils 204, 206 must be at given distance from the display 102 in order to align with the plane (e.g., plane 208) and pupil center points established by the guide markers 108, 110, 112 (as described in connection with FIGS. 1 and 2). Therefore, various distances from the display 102 may be compiled that correlate with various interpupillary distances. Because the location of the guide markers 108, 110, 112 does not change, greater or lesser interpupillary distances are, respectively, greater or lesser distances from the display 102 when they fall within the same plane. By generating this tabulation, or another determinable corresponding mathematical and geometric relationship, the interpupillary distance of an unknown pair of pupils in that plane may be derived by determining the distance between the pupils and the display 102. When the scale of the distance from the camera for objects within the plane is known, the position of the pupils in three-dimensional space is given by their position in an image collected by the camera.

The field of view (FOV) of the camera 104 may be a known quantity. For example, the field of view (FOV) may be known based on the manufacturer and settings of the camera 104. The FOV may alternatively be determined using a calibration object 402, as shown in FIG. 4.

Figure 4:
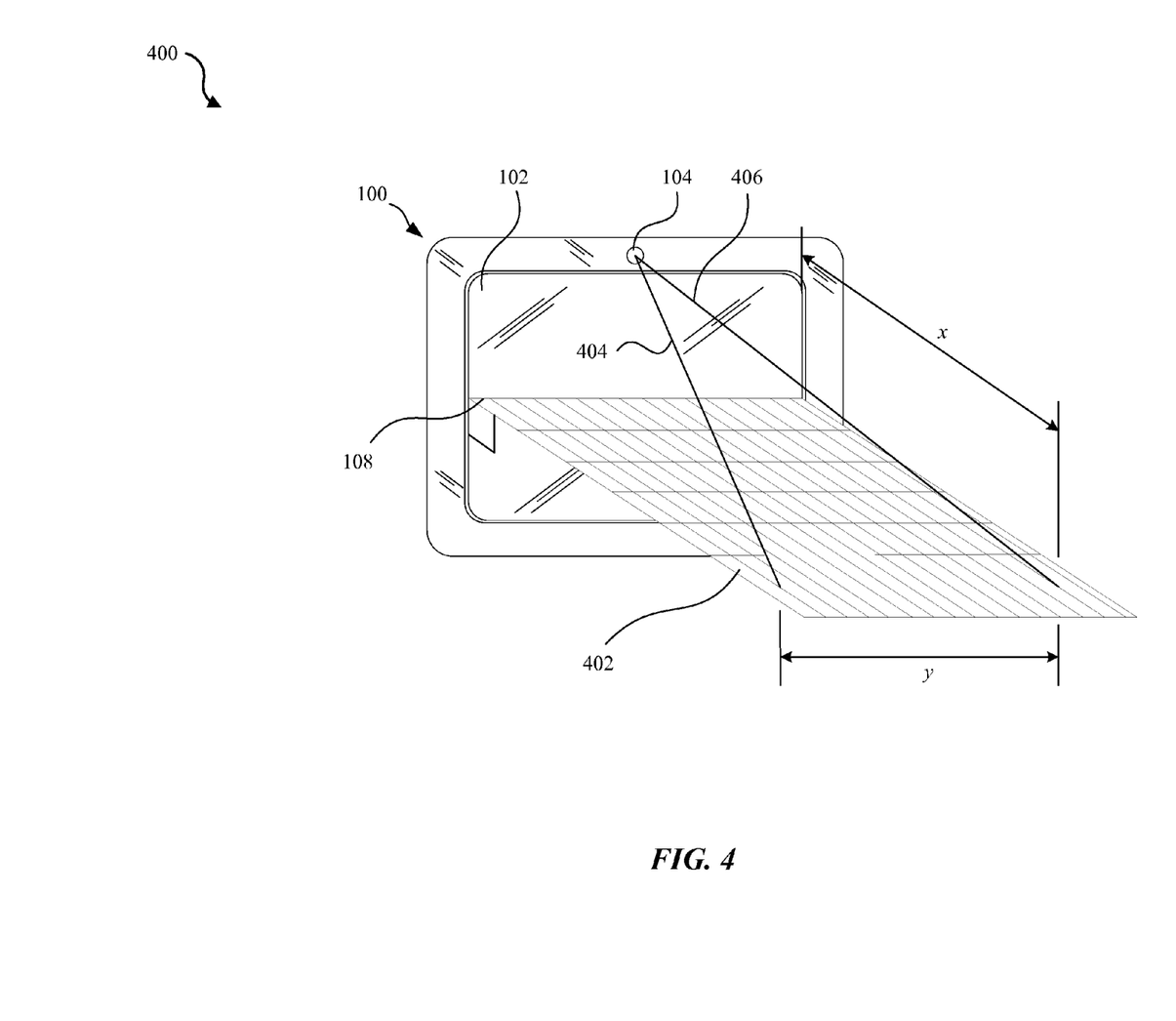
FIG. 4 shows a diagram of a mobile device and a calibration object.

FIG. 4 is a diagram 400 showing a calibration object 402 positioned perpendicular to the display 102 of a mobile device 100. The calibration object 402 may be a flat card or sheet which may be aligned with the guide marker 108 and extend from the display 102 in a manner representative of the plane 208. The surface of the calibration object 402 may be a pattern viewable by the camera 104, such as a grid, ruler, or checkerboard pattern having regularly-spaced intersection points with accurately known or determinable width and length. The calibration object may also beneficially be matte or non-reflective. Thus, when an image is captured of the calibration object 402 in this position, the maximum width of view of the camera 104 on the calibration object 402 (which may be exemplified by projection rays 404, 406) may provide the FOV of the camera 104. If the calibration object 402 pattern is not viewable by the camera 104, a larger object 402 may be needed or the object may need to be repositioned, if possible. For example, in some embodiments, the FOV (in degrees) may be determined using the relationship given by $$FOV° = 2 * \tan^{-1}(y/x),$$

where y is the maximum width of the view of the camera 104 at a distance x measured normal to a flat surface plane from the camera 104, as shown in FIG. 4.

Figure 5:
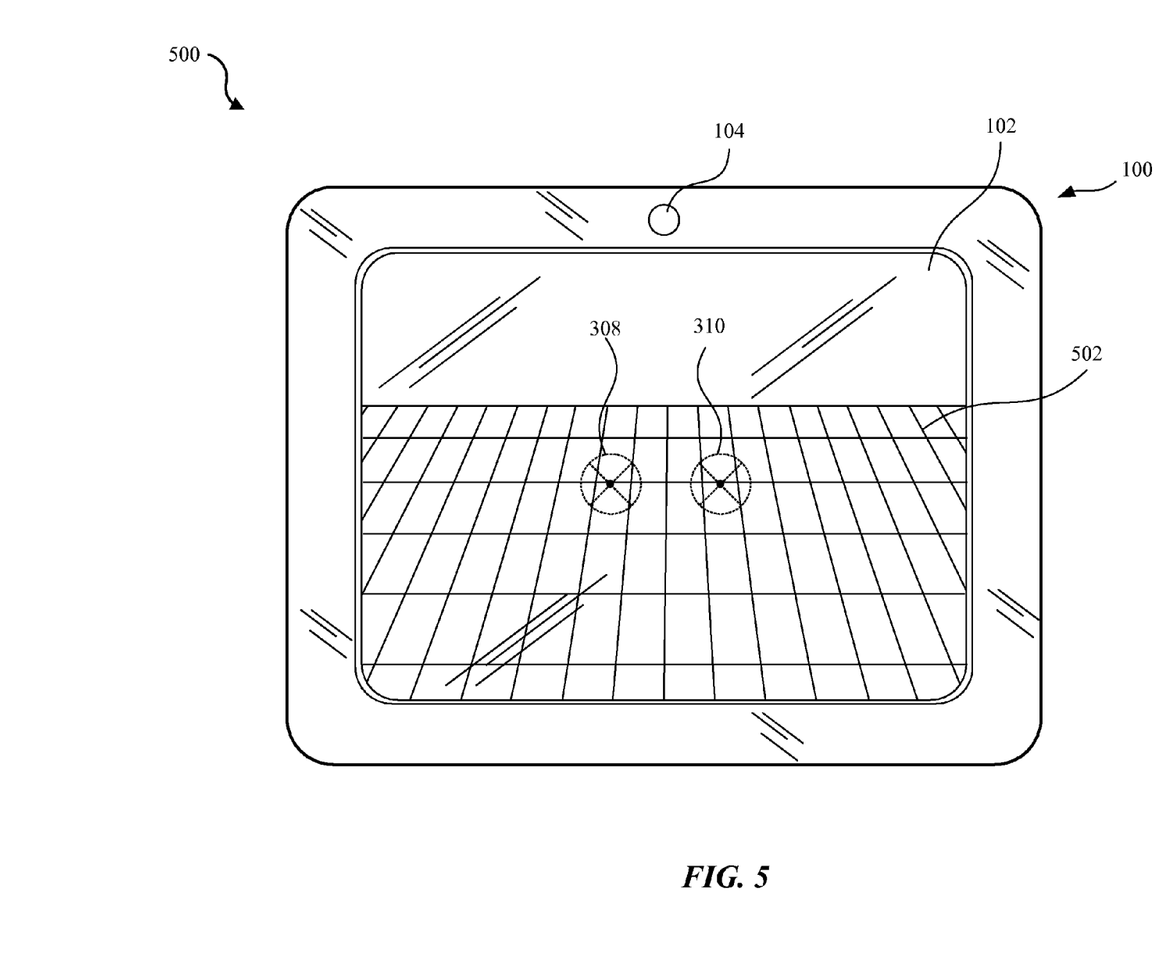
FIG. 5 shows a diagram of a mobile device showing a calibration image.

With this data, the distance between two points in the image (e.g., as provided by the user in FIG. 3) may be converted to the interpupillary distance. For example, the distance between the markers 308, 310 in the image may be compared to the distance between gridlines or other markings on the calibration image 502, as shown in diagram 500 of FIG. 5. Thus, in some embodiments, the distance between the markers 308, 310 may be compared to the markings on the calibration object 402 in the calibration image 502, and the interpupillary distance may be measured with a high degree of accuracy. In some arrangements, the markers 308, 310 are superimposed onto a calibration image 502, as shown in FIG. 5, but in other configurations, the calibration image information may be stored by a memory module and may not be presented on the display 102. Calibration may also feature a step of determining or gathering information regarding the geometric relationship between elements of the device, such as, for example, the distance between the camera 104 and the display 102, guide markers 108, 110, 112, or other portions of the device 100. In yet other configurations, a calibration image or calibration image information may not be used, such as when the scaling of the FOV of the camera 104 may be known or determined without use of a calibration object 402 or calibration image 502.

It will be appreciated by those having skill in the art that the comparison of the position of the markers 308, 310 to calibration information or other scaling information in these embodiments may be done with low levels of processing power, so these embodiments may be implemented in many different kinds of mobile devices, including those having low or limited processing capability. This may also provide the benefit of calculating the interpupillary distance quickly and using low amounts of energy, which can be a particularly important factor in mobile device embodiments.

Figure 6:
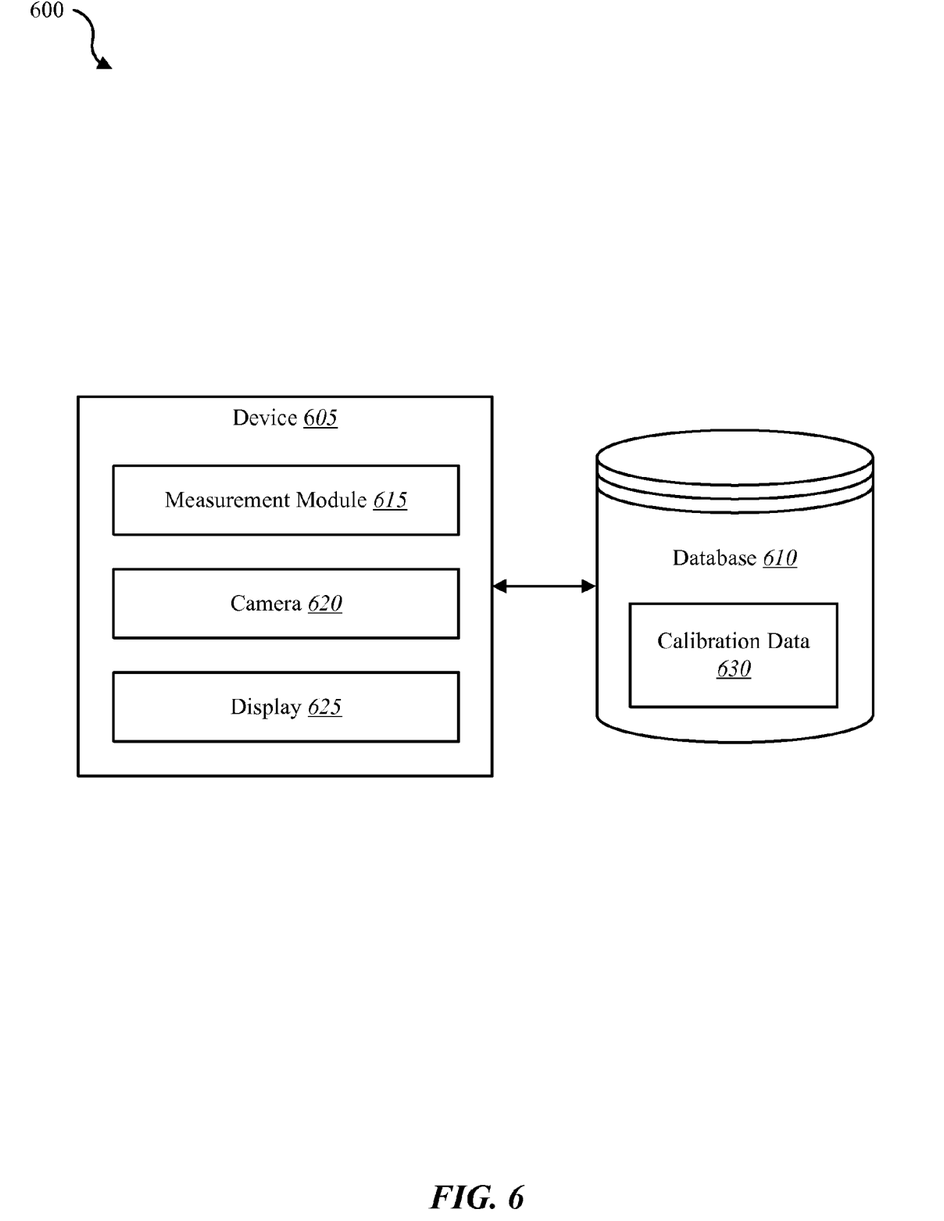
FIG. 6 shows a block diagram of an environment in which the present systems and methods may be implemented.

FIG. 6 is a block diagram illustrating one embodiment of an environment 600 in which the present systems and methods may be implemented. In some embodiments, the systems and methods described herein may be performed on a single device (e.g., device 605). For example, the systems and methods described herein may be performed by a measurement module 615 that may be located on the device 605. Examples of the device 605 include mobile devices, smart phones, personal computing devices, PDAs, computers, servers, etc., as discussed above. The device 605 may be mobile device 100.

In some configurations, a device 605 may include the measurement module 615, a camera 620, and a display 625. The camera 620 may be embodied as camera 104, and the display 625 may be embodied as display 102. In one example, the device 605 may be coupled to a database 610. The database 610 may be internal to the device 605. In another embodiment, the database 610 may be external to the device 605. In some configurations, the database 610 may include calibration data 630. Calibration data 630 may comprise data structures used in the determination of a distance in an image, such as calibration images (e.g., calibration image 502), focal data and field of view data of the camera 620, predetermined interpupillary distance data, and other related information. In one example, the calibration data 630 comprises calibration information for common cameras or mobile devices and the calibration data 630 is accessed based on, e.g., the model of the smartphone or tablet being used to take a measurement.

In one embodiment, the measurement module 615 may measure an interpupillary distance based on an image captured by the camera 620, as described in further detail above. In one example, the interpupillary distance is derived from a user's identification of pupils in a camera-collected image and the calibration data 630. The camera-collected image may be captured by the camera 620 when the pupils of a user are aligned in-plane with a guide marker shown on the display 625.

Figure 7:
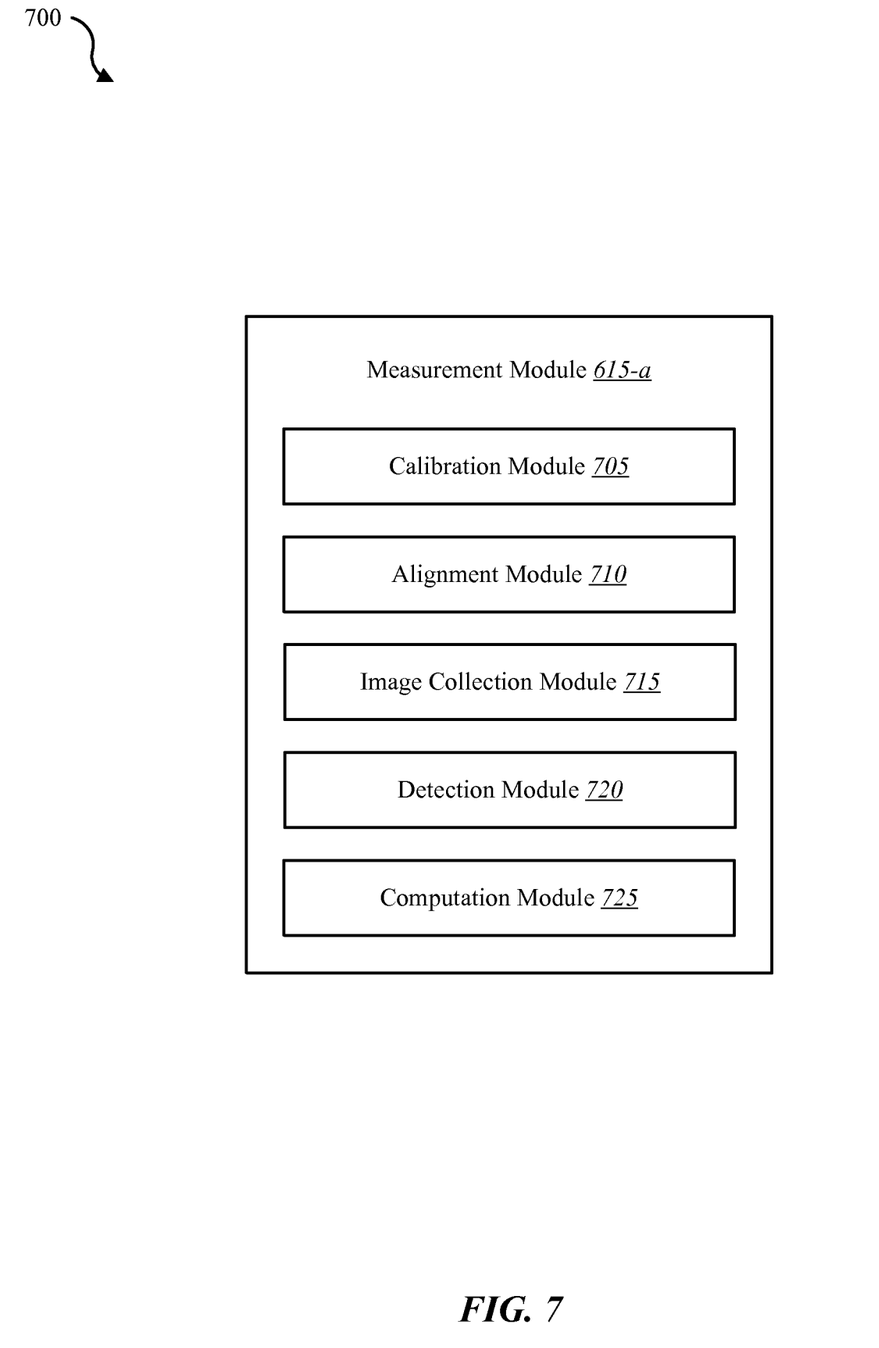
FIG. 7 shows a block diagram illustrating an example of a measurement module.

FIG. 7 is a block diagram 700 illustrating one example of a measurement module 615-*a*. The measurement module 615-*a* may be one example of the measurement module 615 illustrated in FIG. 6. In some configurations, the measurement module 615-*a* may obtain an image (e.g., depicting an interpupillary distance) and compute a measurement of a distance between portions of the image (e.g., the interpupillary distance). In some configurations, the measurement module 615-*a* may include a calibration module 705, an alignment module 710, an image collection module 715, a detection module 720, and a computation module 725. In some arrangements, one or more of these modules may be embodied or combined into a single module.

A calibration module 705 may provide logic for the generation of a calibration image, a calibration grid, or gathering of calibration data. For example, the calibration module 705 may provide for generation of a calibration image as described in connection with FIGS. 4 and 5. Thus, the calibration module 705 may produce a calibration image or calibration information for a camera and display associated with the measurement module 615-*a*, such as the camera 620 and display 625 of FIG. 6. In some embodiments, the calibration module 705 may store or reference calibration information without gathering new calibration information, such as by accessing the database 610.

An alignment module 710 may provide logic for the display of one or more guide markers on a display associated with the measurement module 615-*a*. For example, the alignment module 710 may produce a line or set of dots on the display, such as guide markers 108, 110, 112 of FIG. 1 or other guide markers previously mentioned herein. The alignment module 710 may also include logic to display information on a display such as instructions for alignment of reflections of facial features with elements displayed on the display.

An image collection module 715 may provide logic for operating a camera to capture an image. For example, the image collection module 715 may provide logic for collecting an image using the camera 620 when the device 605 is in a position of alignment of the reflection of a user and guide markers generated on the display 625 by the alignment module 710. The image collection module 715 may therefore instruct a camera to focus on a particular object or distance, or may operate a shutter on the camera, thereby collecting and storing an image viewed by the camera's sensors.

A detection module 720 may provide logic for detecting the location of points in an image. In some embodiments, the detection module 720 may include a facial feature recognition engine. The facial feature recognition engine may analyze the image for facial features or other patterns and then produce output directed to the location of the facial features or other significant points in the image. In at least one embodiment, the detection module 720 may therefore identify the location of two points on an object, such as the pupils of the eyes on a face. In other embodiments, the detection module 720 may prompt a user to locate points of interest (e.g., pupils) in the image with a user prompt on a display or via an audible instruction from a device (e.g., device 605). In some arrangements, the user instructions may be provided as described above in connection with FIG. 3.

A computation module 725 may provide logic for computing the physical distance between points on a face or other body parts captured by the image collection module 715. For example, the computation module 725 use comparisons of the stereo pair created by the reflection in the display (e.g., reflection 114) and the image collected by the camera (e.g., image 302) to estimate the physical distance between two points in the image. The computation module 725 may therefore beneficially implement the computation of distances such as the interpupillary distance using methods described above in connection with FIGS. 3-5.

Figure 8:
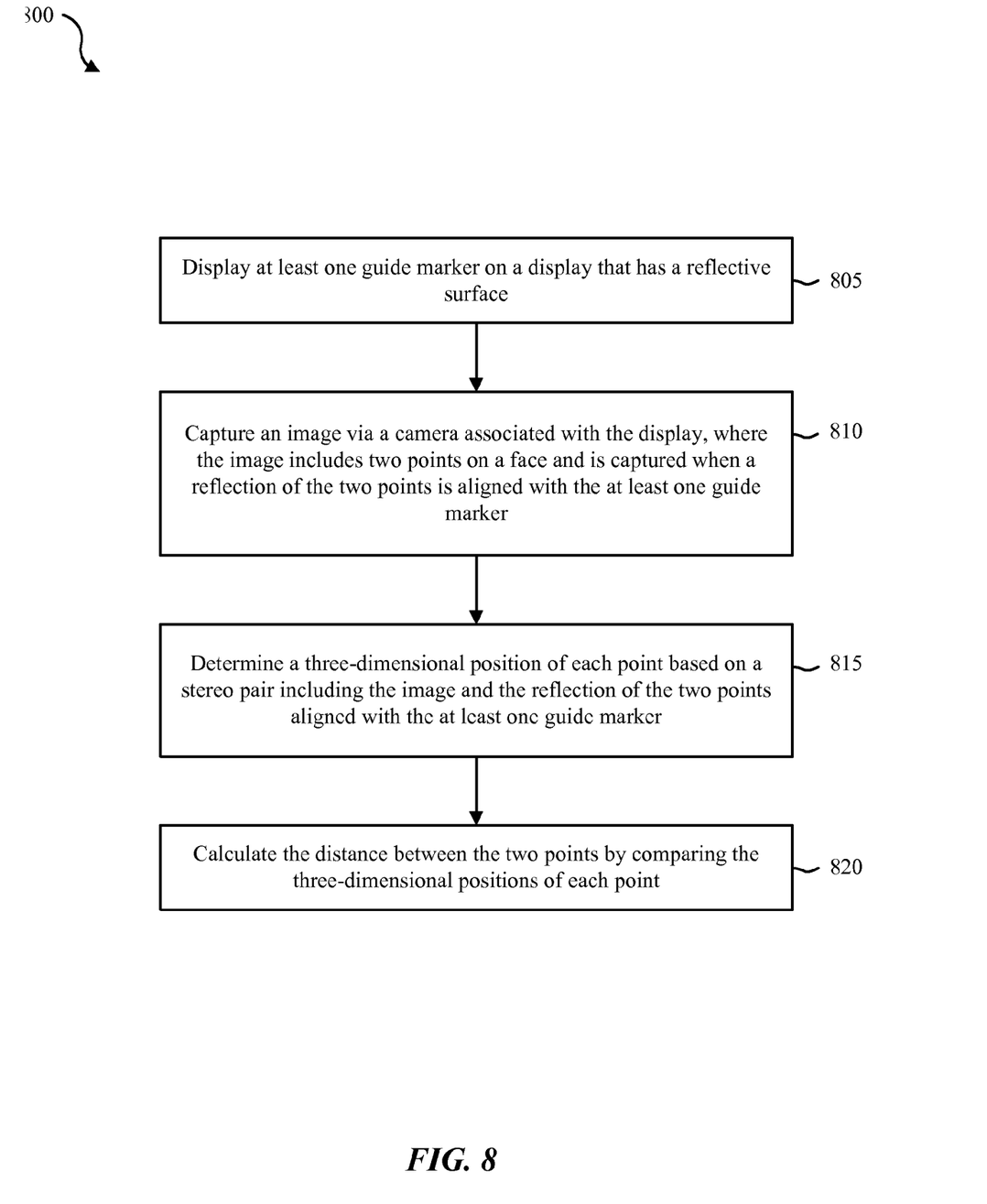
FIG. 8 shows a flow diagram of a method that may be implemented to determine a facial distance.

FIG. 8 is a flow diagram illustrating an example method 800 to determine a distance on a human body using an electronic device. In some configurations, the method 800 may be implemented by the measurement module 615, 615-*a* illustrated in FIGS. 6 and/or 7.

At block 805, at least one guide marker may be displayed on a display that has a reflective surface. At block 810, an image may be captured via a camera associated with the display, where the image includes two points on a body. The image may be captured when a reflection of the two points is aligned with the at least one guide marker. In this block 810, an alterative embodiment may obtain a sequence of photographs or images of the user where the user is in different poses or where the device is in different positions. For example, this may allow the determination of various instances of the interpupillary distances, such as the interpupillary distances for near vision (e.g., at least partially cross-eyed), medium distance vision, and vision directed to infinity. In gathering these various images, the display may need to be placed and aligned at various distances from the user while the user focuses on his reflection in each position (rather than focusing on the device itself, for example). Then, for each image captured, the viewing distance for the user in each image is given as twice the distance between the user and the display (i.e., the distance between the user and his or her reflection).

At block 815, a three-dimensional position of each point may be determined based on a stereo pair including the image and the reflection of the two points aligned with the at least one guide marker. Finally, at block 820, the distance between the two points may be calculated by comparing the three-dimensional positions of each point. This block 820 may include comparing the two points to a calibration image or calibration information, as described in further detail elsewhere in this document.

Figure 9:
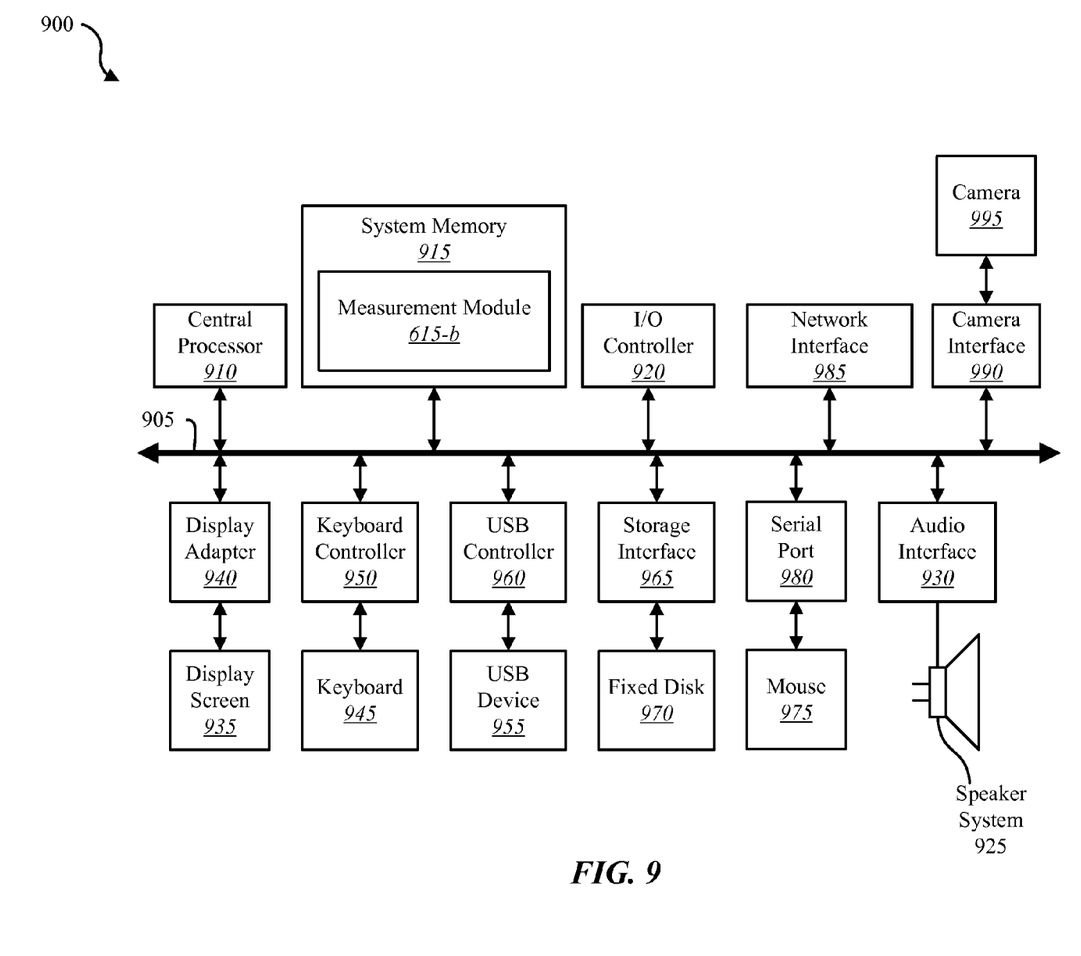
FIG. 9 shows a computer system which may be used in the implementation of the present systems and methods.

FIG. 9 depicts a block diagram of a computer system 900 suitable for implementing at least some of the present systems and methods. For example, the computer system 900 may be suitable for implementing the device 100, 605, illustrated in various figures (e.g., FIGS. 1 through 6). Computer system 900 includes a bus 905 which interconnects major subsystems of computer system 900, such as a central processor 910, a system memory 915 (typically RAM, but which may also include ROM, flash RAM, or the like), an input/output controller 920, an external audio device, such as a speaker system 925 via an audio output interface 930, an external device, such as a display screen 935 (e.g., display 102) via display adapter 940, a keyboard 945 (interfaced with a keyboard controller 950) (or other input device such as a touch screen interface), multiple universal serial bus (USB) devices 955 (interfaced with a USB controller 960), and a storage interface 965. Also included may be a mouse 975 (or other point-and-click device) interfaced through a serial port 980 and a network interface 985 (coupled directly to bus 905) and a camera interface 990 interfacing a camera 995.

Bus 905 allows data communication between central processor 910 and system memory 915, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output System (BIOS) which controls basic hardware operation such as the interaction with peripheral components or devices. For example, the measurement module 615-*b* to implement the present systems and methods may be stored within the system memory 915. The measurement module 615-*b* may be one example of the measurement module depicted in FIG. 6 or 7. Applications resident with computer system 900 are generally stored on and accessed via a non-transitory computer readable medium, such as a hard disk drive (e.g., fixed disk 970) or other storage medium. Additionally, applications can be in the form of electronic signals modulated in accordance with the application and data communication technology when accessed via interface 985.

Storage interface 965, as with the other storage interfaces of computer system 900, can connect to a standard computer readable medium for storage and/or retrieval of information, such as a fixed disk drive 970. Fixed disk drive 970 may be a part of computer system 900 or may be separate and accessed through other interface systems. Network interface 985 may provide a direct connection to a remote server via a direct network link to the Internet via a POP (point of presence). Network interface 985 may provide such connection using wireless techniques, including digital cellular telephone connection, Cellular Digital Packet Data (CDPD) connection, digital satellite data connection, or the like.

Many other devices or subsystems (not shown) may be connected in a similar manner (e.g., document scanners, digital cameras, and so on). Conversely, all of the devices shown in FIG. 9 need not be present to practice the present systems and methods. The devices and subsystems can be interconnected in different ways from that shown in FIG. 9. The operation of a computer system such as that shown in FIG. 9 is readily known in the art and is not discussed in detail in this application. Code to implement the present disclosure can be stored in a non-transitory computer-readable medium such as one or more of system memory 915 or fixed disk 970. The operating system provided on computer system 900 may be iOS®, MS-DOS®, MS-WINDOWS®, OS/2®, UNIX®, Linux®, MAC OS X®, or another like operating system.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon."

What is claimed is:

1. A method of determining a distance on a human body using an electronic device, the method comprising:
    displaying at least one guide marker on a display, the display having a reflective surface;
    capturing an image via a camera associated with the display, the image including two points on a body, wherein when the image is captured a reflection of the two points is aligned with the at least one guide marker;
    determining a three-dimensional position of each point based on a stereo pair, the stereo pair including the image and the reflection of the two points aligned with the at least one guide marker; and
    calculating the distance between the two points by comparing the three-dimensional positions of each point.

2. The method of claim 1, wherein the two points on the body are the centers of each of two pupils of a pair of eyes of a face.

3. The method of claim 1, wherein the distance between the two points is the interpupillary distance.

4. The method of claim 3, wherein the capturing step is repeated to capture a plurality of images, wherein each of the plurality of images correspond with different interpupillary distances.

5. The method of claim 1, further comprising determining calibration information of the camera.

6. The method of claim 5, wherein determining the calibration information of the camera includes:
    capturing an image via the camera, the image including a calibration object having a known geometric relationship to the camera and the display;
    detecting a calibration point on the calibration object in the image; and
    comparing the calibration point of the image to predefined calibration point data to determine the spatial distance between the at least one guide marker and the camera and the field of view of the camera.

7. The method of claim 6, wherein the calibration object includes a pattern of calibration points, the calibration point being detected by detecting at least a portion of the pattern of calibration points.

8. The method of claim 1, further comprising detecting the two points in the image.

9. The method of claim 8, wherein detecting the two points engages a facial recognition engine.

10. The method of claim 1, wherein the three-dimensional position of each point is given by an intersection of a projection ray and a plane extending normal to the reflective surface through at least a portion of the at least one guide marker, each projection ray passing through one of the points and the camera, the points being coincident with the plane.

11. The method of claim 10, wherein the at least one guide marker comprises a line on the display and the line is coincident with the plane defined by the at least one guide marker.

12. A computing device configured to determine a distance on a human body, the device comprising:
    a processor;
    memory in electronic communication with the processor;

computer readable instructions stored by the memory that cause the processing circuit to perform a method comprising:
  displaying at least one guide marker on a display, the display having a reflective surface;
  capturing an image via a camera associated with the display, the image including two points on a body, wherein when the image is captured a reflection of the two points is aligned with the at least one guide marker;
  determining a three-dimensional position of each point based on a stereo pair, the stereo pair including the image and the reflection of the two points aligned with the at least one guide marker; and
  calculating the distance between the two points by comparing the three-dimensional positions of each point.

13. The computing device of claim 12, wherein the two points on the body are the centers of each of two pupils of a pair of eyes of a face, and the distance between the two points is the interpupillary distance.

14. The computing device of claim 13, wherein the capturing step is repeated to capture a plurality of images, wherein each of the plurality of images corresponds with different interpupillary distances.

15. The computing device of claim 12, further comprising determining calibration data of the camera.

16. The computing device of claim 15, wherein determining the calibration data includes:
  capturing an image via the camera, the image including a calibration object having a known geometric relationship to the camera and the display;
  detecting a calibration point on the calibration object in the image; and
  determining the spatial distance between the at least one guide marker and the camera and a field of view of the camera by comparing the calibration point of the image to predefined calibration point data.

17. The computing device of claim 16, wherein the calibration object includes a calibration pattern, the calibration point being detected by detection of the calibration pattern.

18. The computing device of claim 12, further comprising detecting the two points in the image.

19. The computing device of claim 18, wherein detecting the two points engages a facial recognition engine.

20. The computing device of claim 12, wherein the three-dimensional position of each point is given by an intersection of a projection ray and a plane extending normal to the reflective surface through at least a portion of the at least one guide marker, the projection ray passing through the point and the camera, the points coincident with the plane.

21. The computing device of claim 20, wherein the at least one guide marker comprises a line on the display and the line is coincident with the plane defined by the at least one guide marker.

22. A computer program product for determining, by a processor, a distance on a human body, the computer program product comprising a non-transitory computer-readable medium storing instructions thereon, the instructions being executable by the processor to:
  display at least one guide marker on a display, the display having a reflective surface;
  capture an image via a camera associated with the display, the image including two points on a body, wherein when the image is captured a reflection of the two points is aligned with the at least one guide marker;
  determine a three-dimensional position of each point based on a stereo pair, the stereo pair including the image and the reflection of the two points aligned with the at least one guide marker; and
  calculate the distance between the two points by comparing the three-dimensional positions of each point.

* * * * *